United States Patent [19]

Bogen et al.

[11] Patent Number: 5,645,114
[45] Date of Patent: Jul. 8, 1997

[54] DISPENSING ASSEMBLY WITH INTERCHANGEABLE CARTRIDGE PUMPS

[75] Inventors: Steven A. Bogen, Sharon; Herbert H. Loeffler, Arlington, both of Mass.

[73] Assignee: CytoLogix Corporation, Sharon, Mass.

[21] Appl. No.: 251,597

[22] Filed: May 31, 1994

Related U.S. Application Data

[63] Continuation-in-part of Ser. No. 881,397, May 11, 1992, Pat. No. 5,316,452.

[51] Int. Cl.6 ........................................ G01N 1/00
[52] U.S. Cl. .................. 141/145; 141/130; 141/151; 422/64; 422/100
[58] Field of Search ........................ 141/101, 103, 141/104, 130, 144–147, 151, 152; 422/64, 100

[56] References Cited

U.S. PATENT DOCUMENTS

| | | | |
|---|---|---|---|
| 3,768,704 | 10/1973 | Beguin | 222/207 |
| 4,095,722 | 6/1978 | Miller | 222/1 |
| 4,130,224 | 12/1978 | Norman et al. | 222/185 |
| 4,224,032 | 9/1980 | Glover et al. | 422/64 X |
| 4,268,226 | 5/1981 | Morris | 417/332 |
| 4,334,640 | 6/1982 | Van Oberbruggen et al. | 222/207 |
| 4,537,561 | 8/1985 | Xanthopoulos | 417/63 |
| 4,741,259 | 5/1988 | Ogata et al. | 99/279 |
| 4,764,342 | 8/1988 | Kelln et al. | 141/130 X |
| 4,798,580 | 1/1989 | DeMeo et al. | 604/30 |
| 4,824,337 | 4/1989 | Lindner et al. | 417/417 |
| 4,838,887 | 6/1989 | Idriss | 604/891 |
| 4,846,636 | 7/1989 | Danby et al. | 417/413 |
| 4,846,797 | 7/1989 | Howson et al. | 604/154 |
| 4,847,208 | 7/1989 | Bogen | 436/174 |
| 4,967,940 | 11/1990 | Blette et al. | 222/214 |
| 4,974,754 | 12/1990 | Wirz | 222/207 |
| 4,974,952 | 12/1990 | Focht | 359/398 |
| 5,049,359 | 9/1991 | Azuma et al. | 422/64 X |
| 5,073,504 | 12/1991 | Bogen | 436/174 |
| 5,100,030 | 3/1992 | Roggenburg, Jr. et al. | 222/181 |
| 5,232,664 | 8/1993 | Krawzak et al. | 422/64 |
| 5,273,905 | 12/1993 | Muller et al. | 435/286.5 |
| 5,425,918 | 6/1995 | Healy et al. | 422/64 |

*Primary Examiner*—J. Casimer Jacyna
*Attorney, Agent, or Firm*—Hamilton, Brook, Smith & Reynolds, P.C.

[57] ABSTRACT

This invention describes a cartridge pump and dispensing assembly for applications where cartridges containing liquid reagents are interchanged often. The cartridge pump comprises a reagent reservoir which directly empties into a metering chamber. A valve is at each end of the metering chamber. The two valves are aligned in the same direction so as to allow unidirectional liquid flow. The metering chamber is made of a compressible material, such as flexible tubing, so that when an external compression is applied to the chamber, the liquid contained therein is forcibly expelled. As the compression is removed, the metering chamber resumes its former shape and draws liquid into the chamber from the reagent reservoir. A dispensing assembly with electromechanical actuators for compression of the metering chamber and a means for sensing the amount of liquid contained within the reagent reservoir are also shown.

19 Claims, 10 Drawing Sheets

DISPENSING ASSEMBLY WITH INTERCHANGEABLE CARTRIDGE PUMPS

RELATED APPLICATIONS

This application is a Continuation-in-Part of patent application Ser. No. 07/881,397 which was filed on May 11, 1992 now U.S. Pat. No. 5,316,452.

BACKGROUND OF THE INVENTION

This invention relates to a pump mechanism for dispensing small aliquots of a fluid, such as a biological reagent. It may serve as part of an apparatus which dispenses a plurality of reagents to be dispensed in small volumes.

Current methods for dispensing reagents generally use pumps which require the priming of tubing lines leading into and out of a pump. When the pumping is finished, the tubing lines must be flushed before a different reagent can be pumped, lest cross-contamination of reagents occur. Because of the need for priming and clearing tubing lines, such types of pumps are not easily interchangeable.

Pumping systems using a syringe housing ("syringe pumps") are well known to those in the field. The syringe is first filled with a liquid. The liquid can then be accurately dispensed by applying a precise pressure on the plunger, usually by an electromechanical actuator. The distance that the plunger is depressed directly controls the amount of fluid to be dispensed. Such syringe pumps have two advantages: 1) the absence of tubing lines leading into and out of a pump which must be primed and flushed, and 2) a separation of the wetted components from the electromechanical controlling elements.

Such syringe pumps are useful in situations where repetitive dispensing of precise amounts of liquid are required. A drawback of such syringe pumps is that interchanging syringes on a single electromechanical actuator requires that the actuator mechanism be realigned with the position of the syringe plunger that is being inserted. In circumstances where the syringes need to be changed often in order to change the dispensed reagent, the need for repetitive manual intervention to align the electromechanical actuator with the position of the syringe plunger is a disadvantage. This disadvantage will be more acutely felt in a dispensing instrument with many electromechanical actuators.

SUMMARY OF THE INVENTION

A cartridge pump in accordance with the present invention may be used as a component of a movable platform containing a plurality of electromechanical actuators. In this manner, any desired liquid reagent contained in any of the cartridges can be dispensed at any location underneath the platform's reach. Alternatively, the present invention includes a rotor containing reagents and a rotor containing slides that rotate on the same axis. A single actuator is located on a station enabling the slides to be accessed by the reagents. At the end of the working session, the cartridges can be easily replaced with different cartridges using the same electromechanical actuators without the need for aligning electromechanical actuators with the cartridges. This aspect increases the versatility of the dispensing instrument as a whole.

In accordance with an aspect of the present invention, a pump cartridge comprises a reagent reservoir for containing a liquid. The reservoir has a liquid flow outlet at the bottom thereof. A metering chamber is directly connected to the liquid flow outlet of the reagent reservoir. The metering chamber comprises a compressible housing having a non-compressed shape. A one-way inlet valve and a one-way outlet valve are provided at respective ends of the compressible housing and are aligned in the same direction to allow unidirectional flow from the reservoir through the housing. The compressible housing may be compressed for the unidirectional ejection of a volume of liquid from the metering chamber. The compressible housing returns to the noncompressed shape after cessation of compression to draw an additional volume of liquid into the metering chamber.

In a dispensing assembly, a pump cartridge frame may hold the pump cartridge in a fixed position with respect to an actuator capable of compressing the compressible housing of the pump cartridge. Preferably, the actuator is an electromechanical actuator. The dispensing assembly may be mounted on a moveable platform for dispensing various reagents in various sample cells. In one embodiment, a plurality of electromechanical actuators are positioned adjacent to a plurality of receptacles on the frame into which a plurality of pump cartridges can be fit.

The cartridge may have one or more ridges extending outwardly from its external surface to serve as keys in grooves in a supporting frame. Cartridges may be coded by the circumferential positions of ridges to assure that cartridges containing particular reagents are inserted in appropriate locations in the frame.

According to another aspect of the invention, a dispensing assembly comprises an assembly base and a slide rotor adapted to carry a plurality of microscope slides holding tissue samples. This slide rotor is capable of rotating on the assembly base. Further, a reagent rotor adapted to carry a plurality of different reagents sits above the slide rotor and is also capable of rotating on the assembly base.

In preferred embodiments, slide frames are provided for holding the slides in the slide rotor. The slide frames are radially insertable into the slide rotor. These slide frames themselves comprise a slide frame base adapted to support a plurality of slides and containing resistive heating units for heating each one of these slides. A thermocouple can also be provided to detect the temperature of the slides as heated by the resistive heating units. A slide frame housing is adapted to sealably fit over the slide frame base to create cavities over each of the slides and place each of these slides in fluid isolation from each other.

The reagent rotor carries at least one pump cartridge frame that comprises a plurality of receptacles for receiving a plurality of cartridge pumps. These cartridge pumps comprise a reservoir for containing a reagent, a resilient metering chamber in fluid communication with an outlet of the reservoir and a one way inlet valve and one way outlet valve at each end of the resilient metering chamber.

The dispensing assembly further comprises a dispensing station positioned adjacent to each of the slide rotor and the reagent rotor. This dispensing station comprises an actuator adapted to deform the resilient metering chamber in a cartridge pump so that a volume of reagent contained in that cartridge pump is ejected into a slide underneath the cartridge pump held by the slide rotor. This dispensing station also includes a plurality of pressurized rinse bottles and rinse tubes that extend from the rinse station above the slides held by the slide rotor. As such, they can convey rinsing solutions by the opening of pinch valves to the slides underneath the ends of the rinse tubes. Still further, the dispensing station includes a vacuum bottle and vacuum hose that is extendable into a cavity above the slides on the slide rotor to enable removal of rinse solutions covering the slides.

According to another aspect, the reagent reservoir of the cartridge pumps may contain a plunger above the liquid in the reagent reservoir. The plunger is capable of moving within the reservoir as liquid is drawn out of the reservoir through the liquid flow outlet. Preferably, the plunger has a frictional force against the inner wall of the reservoir which is greater than the gravity pressure of the liquid in the reservoir in order to prevent spontaneous dripping of the liquid out of the outlet valve. Alternatively, the outlet valve in its normally closed position may itself have an opening pressure which is greater than the gravity pressure applied by the liquid in the reservoir. Alternatives to the plunger include a one-way valve at the top of the reservoir, a rolling diaphragm at the top of the reservoir and a small aperture at the top of the reservoir.

To reduce the flow velocity of liquid during ejection, a nozzle with an inner diameter which is greater than the opening diameter of the outlet valve may be positioned below the outlet valve.

To absorb some of the initial force upon impact of the actuator against the tubing, the actuator may be a compressible piston hammer mounted on a piston arm.

The interchangeable pump cartridge of the present invention can be accepted into a dispensing assembly with an electromechanical actuator regardless of the amount of liquid in the cartridge reservoir. The cartridge maintains a separation of the wetted and electromechanical components and does not require priming of tubing lines before and after pumping. Moreover, it may be produced inexpensively and therefore can be disposed of when the reagent in the cartridge is exhausted. As a further advantage over syringe pumps, the cartridge pump of the present invention allows for dispersing of relatively small, precisely metered volumes.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENT

Figure 1:
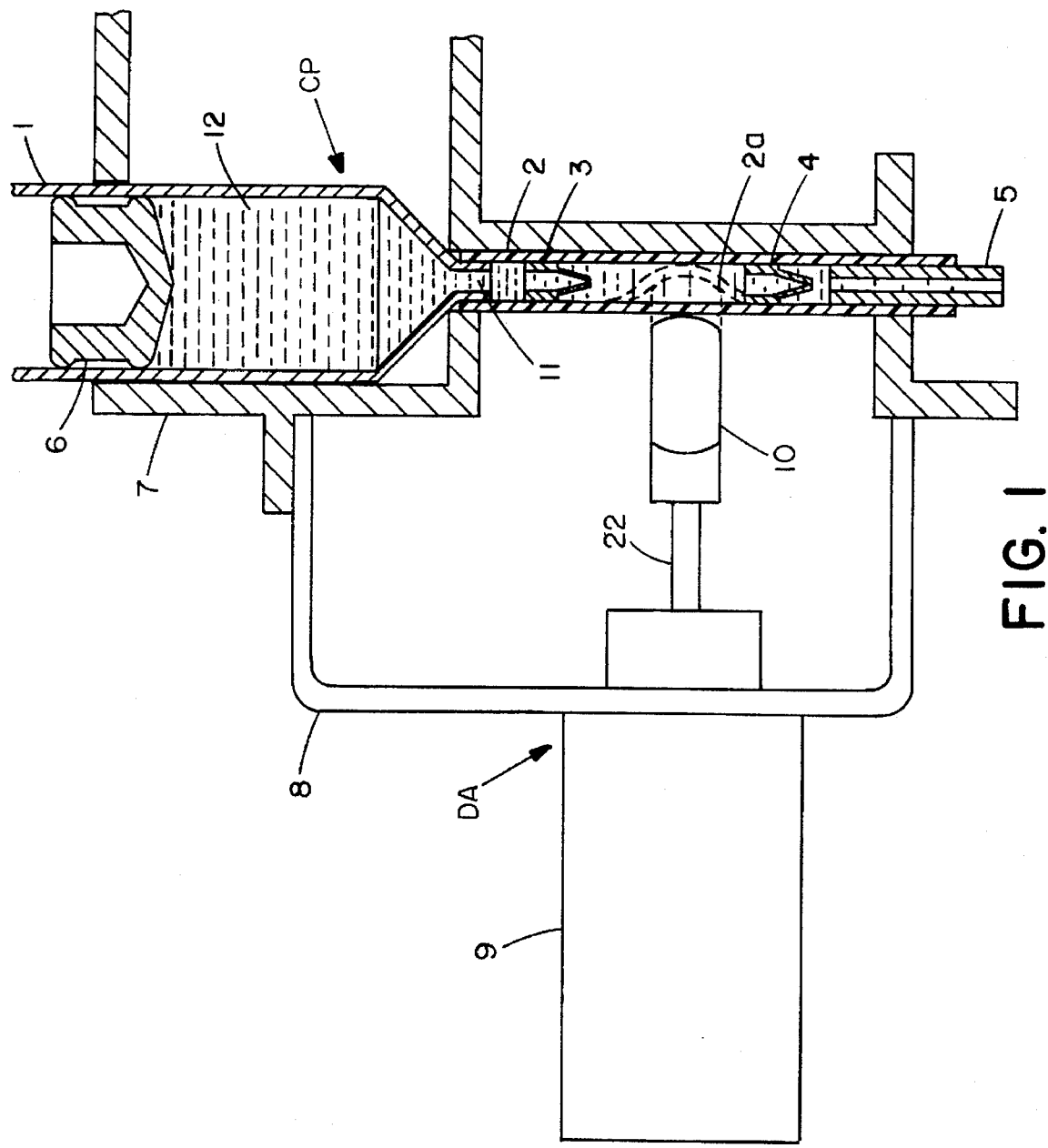
FIG. 1 is a cross-sectional view of the pump cartridge and dispensing actuator mounted on a frame.

Referring to FIG. 1, the cartridge pump CP comprises a pump cartridge reservoir 1 in the shape of a cylindrical barrel. The cartridge reservoir 1 has a lower outlet 11 which is directly connected to a metering chamber comprised of a segment of compressible tubing 2, an inlet valve 3, and an outlet valve 4. The distance between the inlet valve 3 and the outlet valve 4, and the inner diameter of the tubing 2 defines a volume which can be filled with a liquid. A nozzle 5 is placed below the outlet valve 4 for the purpose of decreasing the flow velocity of the liquid. The cartridge reservoir contains a volume of liquid 12 which is sealed from above by a sliding plunger 6. The cartridge reservoir 1, inlet valve 3, outlet valve 4, plunger 6, metering chamber 2, and nozzle 5 are the components of the cartridge pump CP.

In a first embodiment of a dispensing assembly, the cartridge pump CP rests on a rectangular frame 7 which can be made of plastic. A single rectangular frame 7 can hold a plurality of cartridge pumps CP. The rectangular frame 7 can be removed from the chassis 8 by simply lifting the frame, thereby lifting all the cartridge pumps with it. In this manner, the wetted components can be easily separated from the electromechanical components.

The first embodiment dispensing assembly further includes dispensing actuators DA. Each dispensing actuator DA comprises a solenoid 9, arm 22, and rubber hammer 10. When an electrical current is applied to the solenoid 9, the arm 22 extends forcefully, thereby pressing the rubber hammer 10 against the outer wall of the metering chamber tubing 2. This action deforms the tubing, causing the compressible tubing to assume a compressed shape 2a. Since the total volume inside the metering chamber between the valves 3 and 4 is decreased, a volume of liquid is expelled in the direction defined by the valves 3 and 4. In FIG. 1, the valves are shown as allowing fluid in the downward direction only. Since the diameter of the outlet valve 4 leaflets is comparatively narrow relative to the diameter of the tubing 2, the fluid has a high flow velocity. This results in a forceful squirting of the liquid. This aspect is often undesirable, since it may lead to splattering of the liquid if the object surface of the fluid is situated immediately below. Therefore, the nozzle 5 is placed below the outlet valve 4. The nozzle has an inner diameter greater than the diameter of the outlet valve 4 leaflets. This aspect causes the high velocity fluid to first accumulate in the space above and within the inner aspect of the nozzle. The liquid thus exits the nozzle 5 at a slower velocity, ideally in a dropwise manner.

The rubber hammer 10 is also compressible in order to further decrease the flow velocity of the liquid. Most solenoids tend to extend suddenly and forcefully. This results in a very rapid compression of the tubing 2. In order to decrease this rate of compression, the solenoid arm is fitted with a compressible rubber hammer 10 which absorbs some of the initial force upon impact with the tubing 2.

The tubing 2 can be made of silicone rubber, vinyl, polyurethane, flexible polyvinyl chloride (PVC) or other synthetic or natural resilient elastomers. Such types of tubing are commonly used for peristaltic pumps. The valves can be obtained from Vernay Laboratories, Inc., Yellow Springs, Ohio, 45387 (part #VL 743-102).

When the electrical current is removed from the solenoid 9, the arm 22 and rubber hammer 10 is retracted from the surface of the tubing 2. The tubing in the compressed position 2a thereby reverts back to its native position 2 because of the resiliency of the tubing. The reversion of the tubing to its native position results in a negative pressure being created within the metering chamber, causing liquid 12 to be drawn from the pump reservoir 1 into the metering chamber. The metering chamber is therefore automatically primed for the next pump cycle.

Figure 2:
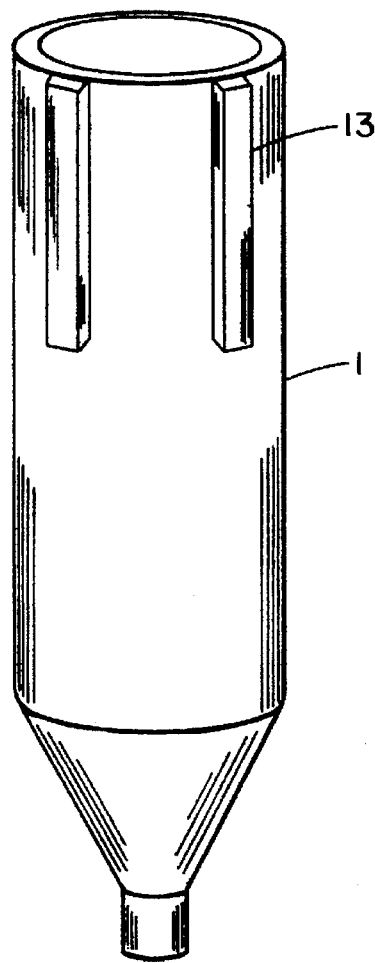
FIG. 2 is a perspective view of the pump cartridge reservoir.

Referring to FIG. 2, the outer aspect of the pump cartridge reservoir 1 has longitudinal ridges 13. These ridges fit into grooves in the frame 7, see FIG. 1, in a lock and key fashion. Different cartridges are manufactured with different patterns of ridges in order to identify the contents. In this manner, any particular cartridge will fit only into a position of the frame with a corresponding pattern of grooves. This feature will prevent the possibility of the operator placing the cartridge in an unintended position of the frame.

Figure 3:
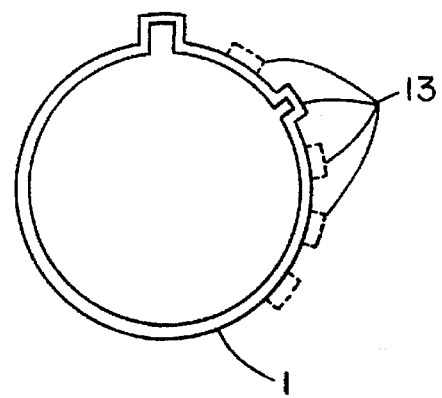
FIG. 3 is a view from above of the pump cartridge.

Referring to FIG. 3, this shows the variety of possible positions for ridges 13 on the outer surface of the pump cartridge reservoir 1.

Figure 4:
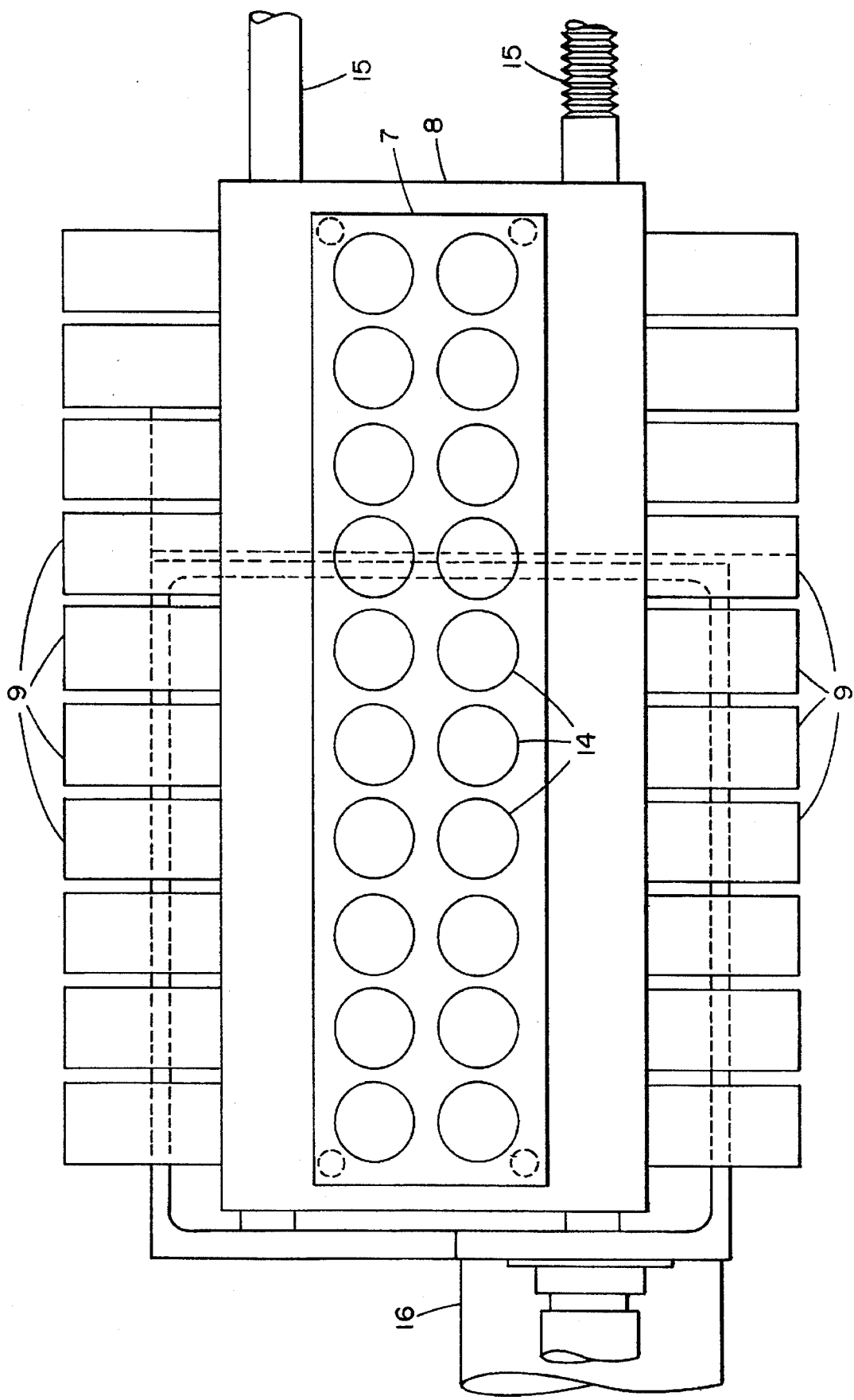
FIG. 4 is a view from above of a plurality of pump cartridges mounted on a first embodiment dispensing assembly including a rectangular frame and chassis of an X-Y axis robot.

Referring to FIG. 4, this shows the first embodiment of the dispensing assembly comprising a rectangular frame 7 having plurality of slots 14 for cartridge pumps in position on the chassis 8 a different dispensing actuator DA being associated with each cartridge pump CP. The chassis is mounted on a pair of cylindrical bars 15. In this case one of the bars is threaded and attached to a motor 16. Alternatively, a cable drive may be provided. The motor can be a conventional stepping motor or servo motor and driven by a computer-generated signal through an electronic interface.

Figure 5:
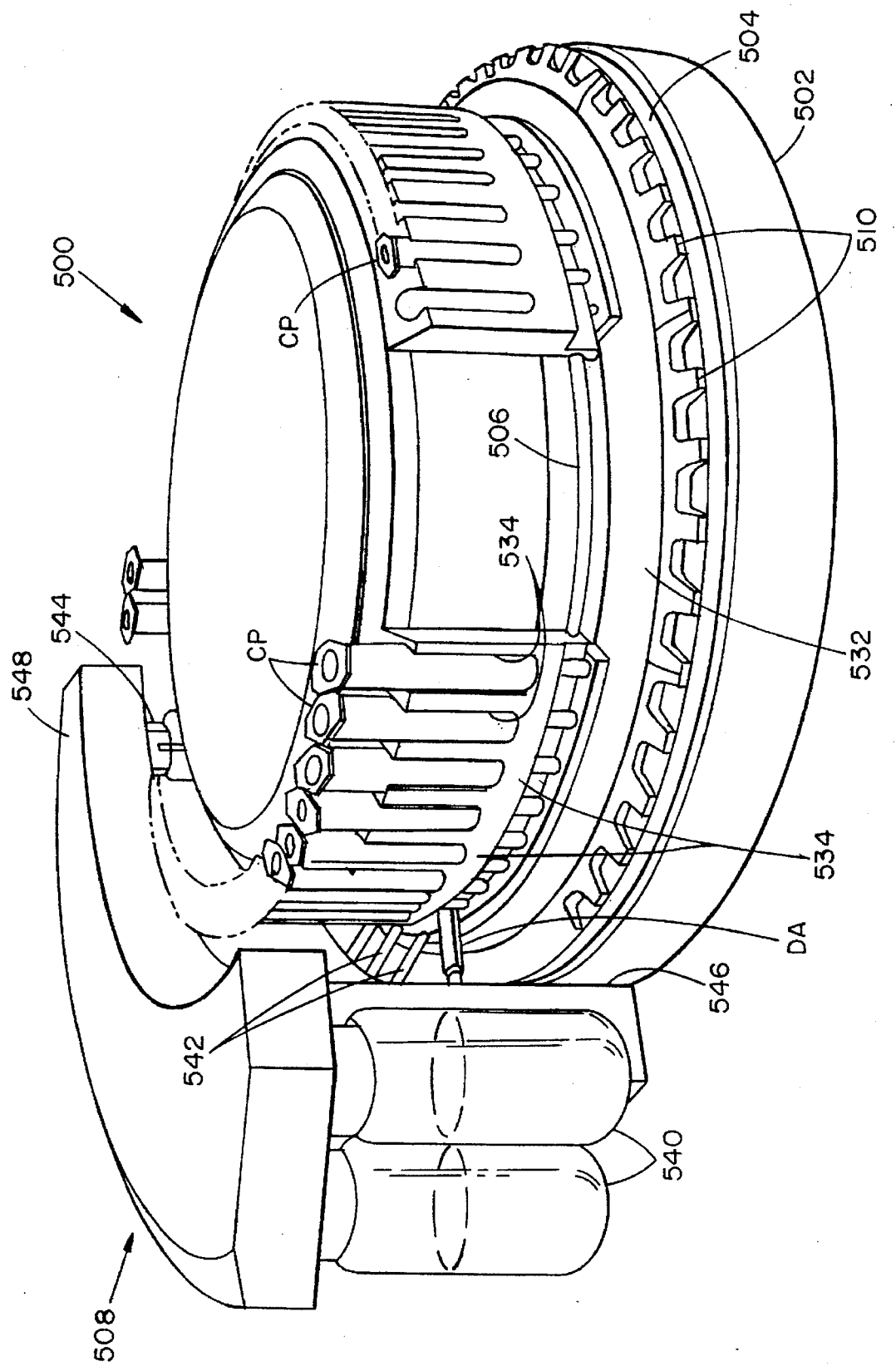
FIG. 5 is a perspective view of a dispensing assembly of a second embodiment of the invention.

FIG. 5 shows a second embodiment 500 of a dispensing assembly in perspective. Generally, the dispensing assembly 500 comprises a substantially circular assembly base 502, a slide rotor 504 rotatable on the assembly base 502, a reagent rotor 506 also rotatable on the assembly base, and a dispensing station 508.

Figure 6:
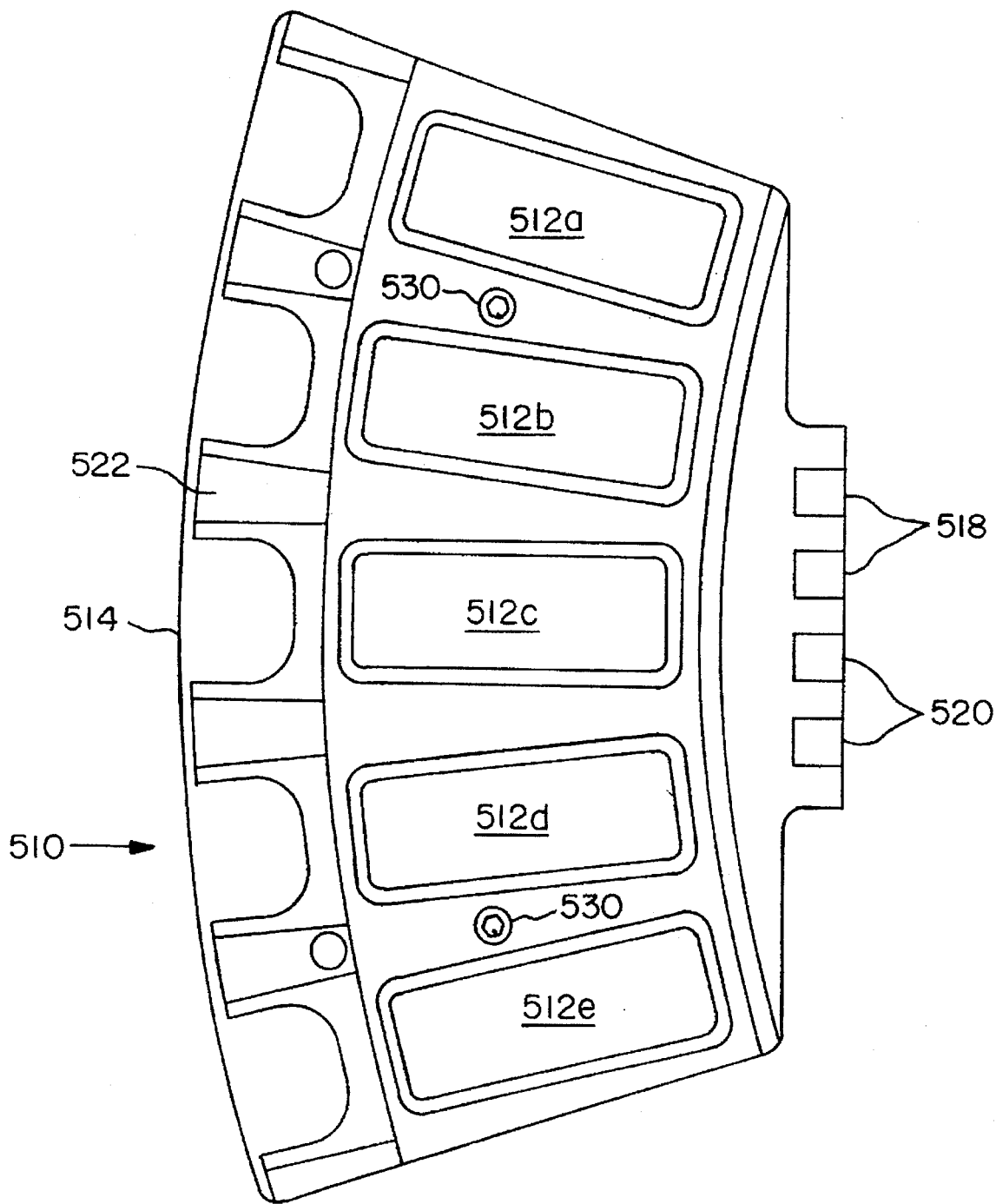
FIG. 6 is a top view of a slide frame for providing five sealed cavities above five different slides holding tissue samples.
Figure 7:
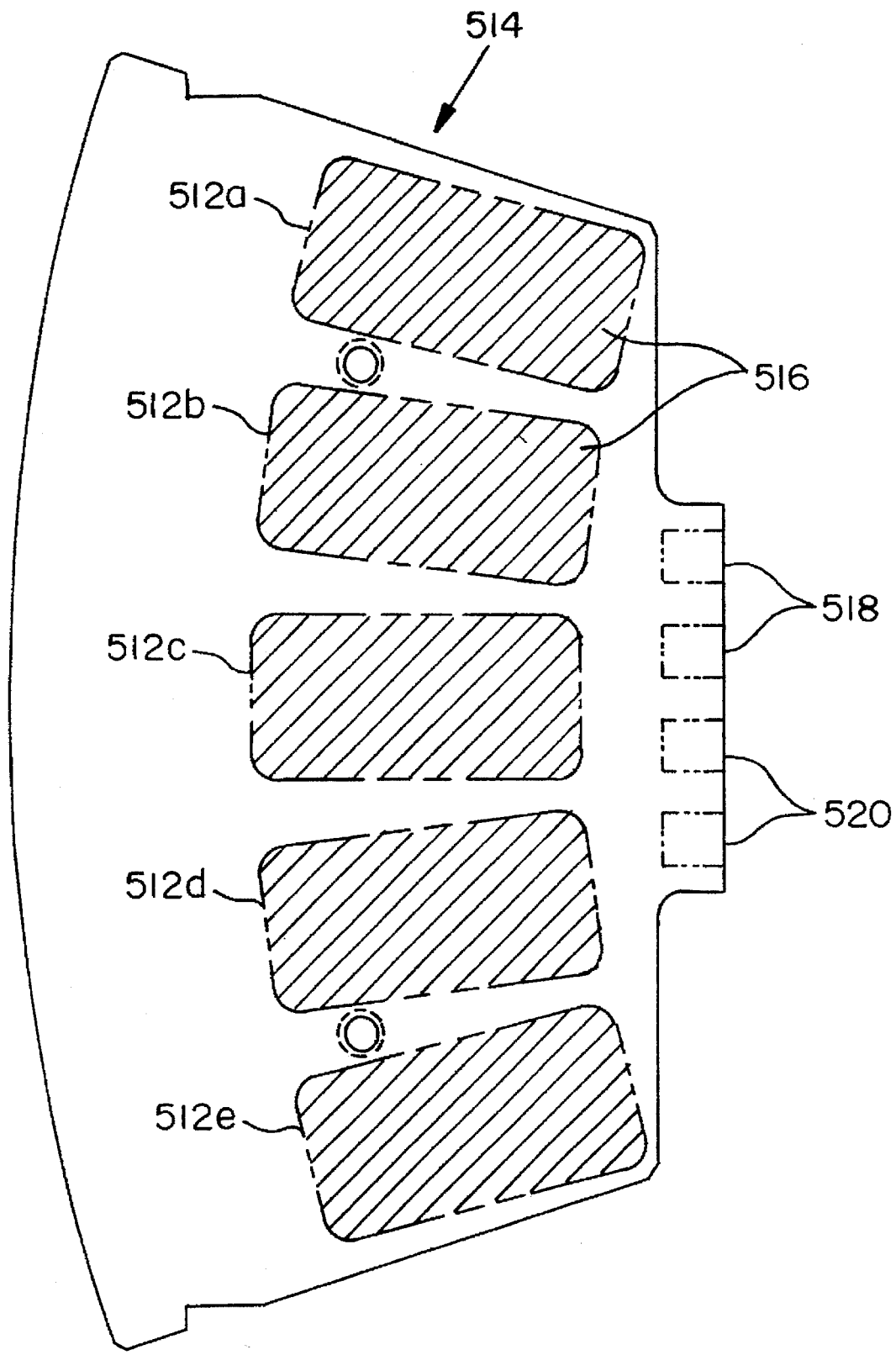
FIG. 7 is a top view of a slide frame base.
Figure 8:
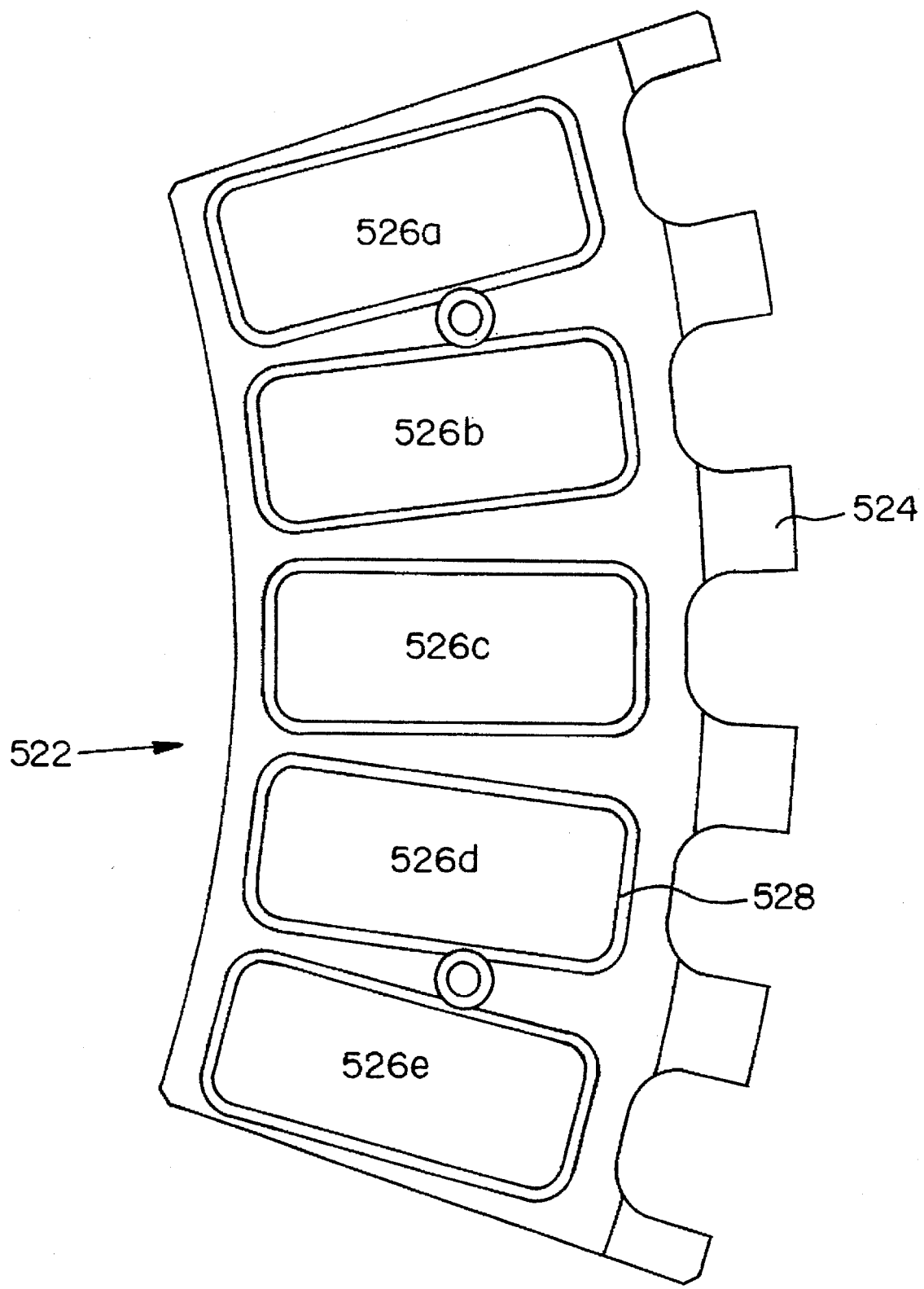
FIG. 8 is a top view of a slide frame housing.

The slide rotor 504 is driven to rotate by a servo motor (not shown) and carries ten slide frames 510 that are radially asserted into and detachable from it. A top view of single slide frame 510 is shown in FIG. 6. Here, a different slide holding a tissue sample is held in each slide position 512a–512e. The slide frame 510 comprises a slide frame base 514 shown in FIG. 7. The slide frame base includes a plurality of heated areas 516 which underlie each of the slide positions 512a–512e and incorporate resistive heating elements, not shown. The heating elements are integrally formed in the slide frame base 514. Electricity for powering the elements is provided into the slide frame 510 from the assembly base 502 via first and second contacts 518. Further, third and fourth contacts 520 enable temperature sensing of the heated areas via thermocouples also integrally formed in the slide frame base 514. Adapted to overlay the slide frame base is a slide frame housing 522. FIG. 8 is a top view of the slide frame housing 522 showing essentially a rigid plastic or metal frame 524 with five oval holes 526a–526e corresponding to each of the slide positions 512a–512e. A silicon rubber gasket 528 is also provided under the plastic frame 524. Returning to FIG. 6, the slide frame housing 522, including the gasket 528 and plastic frame 524, is bolted onto the slide frame base 514 by two Allen bolts 530 to provide individual sealed cavities approximately 0.2–0.4 inches deep over each tissue sample slide placed at each of the slide positions 512a–512e. As a result, a total of 3 ml of reagents and/or rinses can be placed in contact with the tissue samples of each one of the slides but a maximum quantity of 2 ml is preferable. Since the silicone gasket 528 is compressed by the plastic frame 522 against the slide frame base 514, the cavities over each of the frame positions are mutually sealed from each other.

Returning to FIG. 5, above the slide rotor 504 is a non-rotating slide cover 532. This disk-like structure rides above the slide rotor 504 but does not turn with the slide rotor. Basically, it forms a cover for all of the tissue samples held in each of the slide frames 510 so that evaporation of reagents or rinses contained on the slides can be inhibited and also so that environmental contamination of the tissue samples is prevented.

Figure 9:
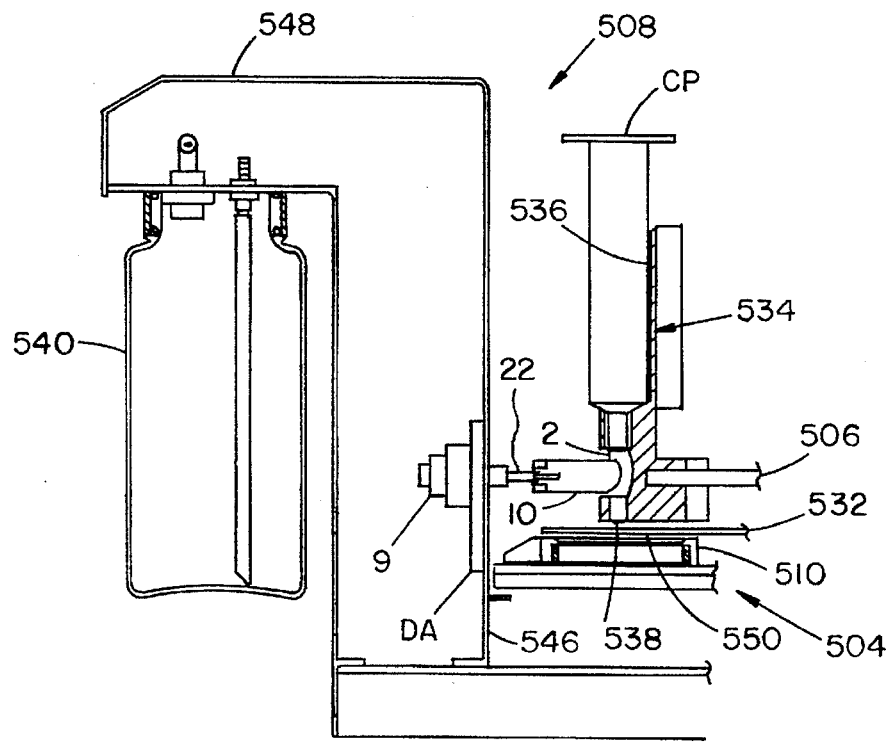
FIG. 9 is a side cross-sectional view showing the dispensing actuator of the dispensing station and an exemplary cartridge pump being engaged by the dispensing actuator.

Positioned above the slide rotor 504 is the reagent rotor 506. This reagent rotor 506 is similarly adapted to rotate on the assembly base 502 and is driven by another servo motor (not shown) so that the reagent rotor 506 and slide rotor 504 can rotate independently from each other. The reagent rotor 506 is adapted to carry up to ten arcuate cartridge frames 534. These arcuate cartridge frames are detachable from the reagent rotor 506 and can be selectively attached at any one of the ten possible points of connection. Each arcuate cartridge frame 534 is capable of carrying five of the reagent cartridge pumps CP. A cross sectional view illustrating the arcuate cartridge frame as shown in FIG. 9. As illustrated, the reagent cartridge pump CP is vertically insertable down into a slot 536 in the arcuate cartridge frame 534 so that the nozzle tip 538 extends down below the cartridge frame and the meter chamber tubing 2 is exposed. The arcuate cartridge frame 534 including any cartridge pumps CP is then slidably insertable onto the reagent rotor 506.

Generally, the dispensing station 508 comprises a dispensing actuator DA for engaging the meter chamber tubing 2 of any one of the reagent cartridge pumps CP in any slot in any one of the arcuate cartridge frames 534. Further, the dispensing station 508 includes rinse bottles 540 that can supply rinses into any one of the slides on any one of the slide frames 510 via rinse tubes 542, and a rinse removal vacuum 544 including a vacuum tube that is extendable down into any one of the cavities in the slide frames 510 to remove rinse or reagent.

Specifically, the dispensing station 508 includes a station frame that has a front wall 546 generally following the curvature of the assembly base 502. The station frame also includes a horizontal top wall 548 continuous with the front wall 546 and from which rinse bottles 540 are hung. The front wall 546 of the station housing supports a single dispensing actuator DA. As best shown in connection with FIG. 9, the dispensing actuator DA includes a solenoid or linear stepping motor 9, an arm 22, and a compressible rubber hammer 10 as described in connection with the dispensing actuator illustrated in FIG. 1. Use of a linear stepping motor instead of a solenoid somewhat negates the necessity of the rubber hammer being highly compressible since the rate of extension of linear stepping motors can be controlled to a slow speed. Because only a single dispensing actuator is required in the second embodiment, more expensive alternatives such as the linear stepping motor are preferable. As another possible alternative, the reciprocating hammer of the dispensing actuator could take the form of a cam, driven by a rotary motor, that engages the compressible tubing so that rotation of the cam will deform the compressible tubing.

Upon actuation of the solenoid 9, the rubber hammer 10 extends outwardly to engage the compressible tubing 2 of the particular cartridge pump CP that has been rotated into position in front of the dispensing actuator DA on the reagent rotor 504. The liquid dispensed from the pump cartridge CP by the action of the dispensing actuator DA falls down through a hole 550 formed in the slide cover 532 into the particular medical slide that has been brought into position in front of the dispensing actuator DA by the rotation of the slide rotor 504. In this way, any one of fifty slides, which the slide rotor 504 is capable of carrying, can be accessed and treated with any one of fifty different reagents that the reagent rotor 506 is capable of carrying in the cartridge pumps CP by properly rotating both the reagent rotor and the slide rotor. By this method both the reagent cartridge pump CP carrying the desired reagent and the slide which the operator intends to receive this reagent are brought to circumferential position of the dispensing actuator DA.

Figure 10:
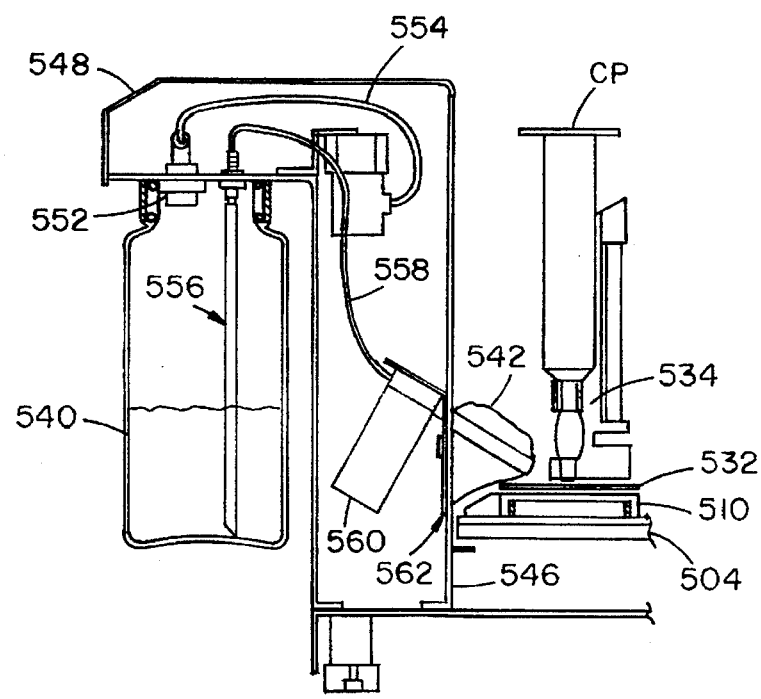
FIG. 10 is a side cross-sectional view of a rinse device housed in the dispensing station.

The dispensing station 508 also carries up to eight different rinses that can be delivered through rinse tubes 542 to any one of the slides held on the slide rotor 504. As shown in FIG. 10, the rinse bottles 540 are screwed into a female threaded cap 552 secured to the underside of the horizontal top wall 548 of the station frame. Compressed air is from a compressor 554 is provided into each one of the rinse bottles 540. The pressure above the rinse then enables the rinse to be forced out through the dip tube 556 through rinse hose 558 when a pinch valve 560 is opened. Depending on the length of time that the pinch valve is opened, a predetermined amount of rinse can be provided out through the rinse tube 542 into the particular medical slide that has been brought underneath the rinse tube end 562 by the rotation of the slide rotor. Eight different rinse tubes 542 corresponding to each rinse bottle 540 and each controlled by a separate pinch valve. Eight holes are provided in the slide cover 532 underneath the ends of the rinse tubes 542 so that the rinse can reach the slides.

Figure 11A:
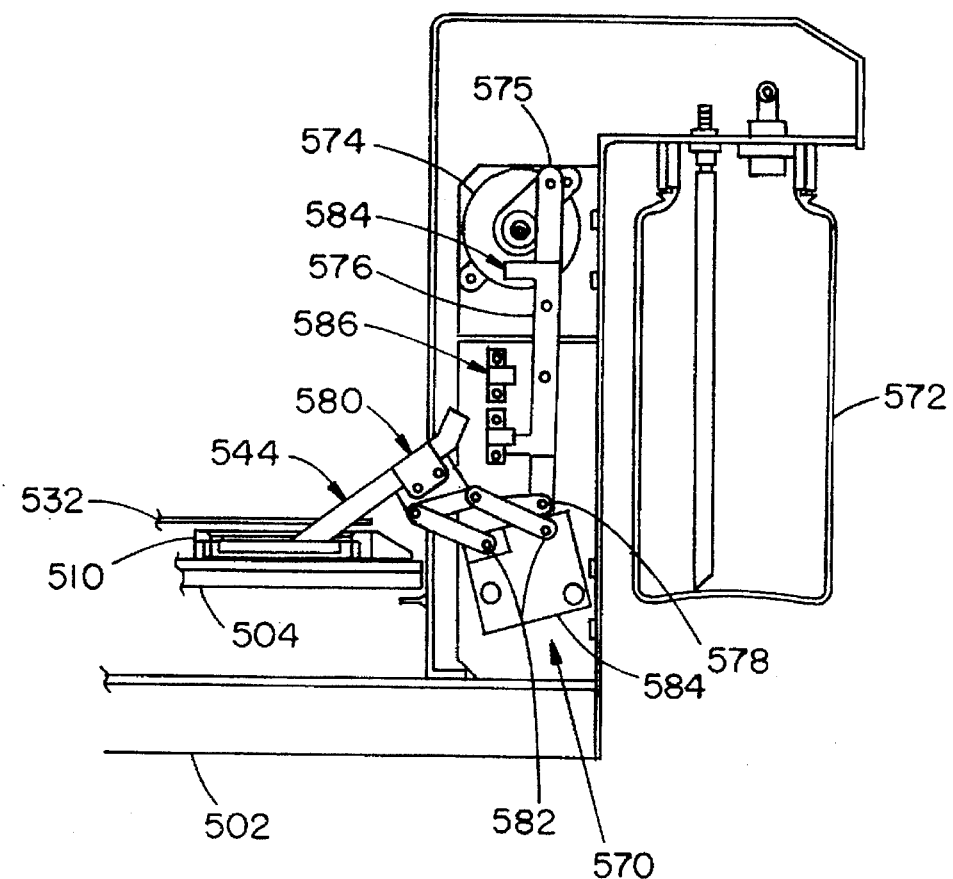
FIGS. 11a and 11b are side cross-sectional views of a vacuum hose and transport mechanism for removing rinse and reagent from slides contained on the slide rotor.

Returning to FIG. 5, also provided on the vertical wall 546 of the station housing is an extendable vacuum hose 544. As more completely shown in cross section in FIG. 11A, the vacuum hose 544 is supported by a hose transport mechanism 570 that allows the vacuum hose 544 to be extended down into a cavity of a slide frame 510 to remove any rinse and reagent covering the tissue sample of the slide. Specifically, the suction is created by a partial vacuum generated in vacuum bottle 572 by a compressor, not shown. Consequently, the rinse and reagent is sucked in through the vacuum hose 544 and into the vacuum bottle when the vacuum hose transport mechanism 570 brings the vacuum hose end in contact with the rinse and/or reagent in cavity of the slide frame 510.

Figure 11B:
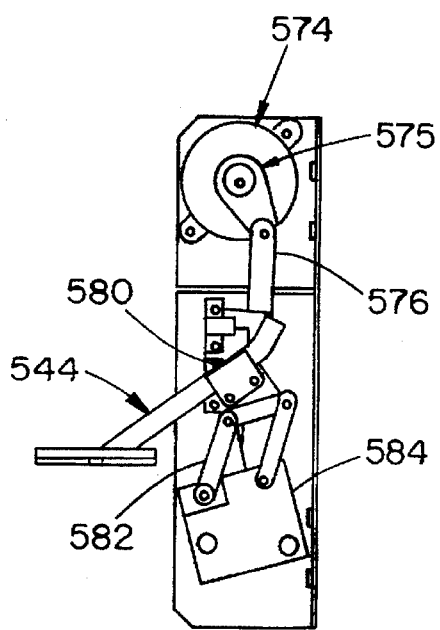

The vacuum hose transport mechanism comprises a motor 574. A reciprocating link 576 is attached to a crank arm 575 so that the rotation of the motor 574 causes the reciprocating link 576 to traverse in a vertical direction. A bottom portion of the reciprocating link 576 is connected to a lever 578 that is pivotally attached to the station frame. The other end of this lever is connected to a vacuum hose clamp 580 that is connected via to pivot arms 582 to a plate 584 rigidly attached to the station frame. The net effect of these connections is that when the motor 574 is rotated, the slide arm 576 descends in the vertical direction. Thus, the lever 578 is pivoted clockwise around its fulcrum causing the hose clamp 580 to pivot up and away on the two pivot arms 582 from the slide as shown in FIG. 11b. The motor is automatically turned off as the slide reaches its two extreme ends of movement by the contact of the electrical terminals 584 of the slide to the contact plates 586 connected to the station frame.

A microprocessor, not shown, controls the entire dispensing assembly 500. That is, an operator programs the microprocessor with the information such as the location of reagents on the reagent rotor and the location of slides on the slide rotor. The operator then programs the particular histochemical protocol to be performed on the tissue samples. Variables in these protocols can include the particular reagent used on the tissue sample, the time that the tissue sample is allowed to react with the reagent, whether the tissue sample is then heated to exposed or develop the tissue sample, the rinse that is then used to deactivate the reagent, followed by the subsequent removal of the rinse and reagent to allow subsequent exposure to a possibly different reagent. The dispensing assembly enables complete random access, i.e. any reagent to any slide in any sequence.

An important aspect of the above-described invention is its ability to retain the fluid until such time as the solenoid hammer 10 presses on the metering chamber tubing 2. As will be noted from FIG. 1, both one-way valves 3 and 4 are aligned in the same direction, allowing only downward flow. It was found during construction that using valves with a low opening ("cracking") pressure resulted in the liquid dripping out of the nozzle. There are two solutions to this problem. The most obvious is to use valves with an opening pressure greater than the pressure head of liquid. In this manner, the outlet valve 4 will not allow fluid exit until a certain minimum force is applied which is greater than the pressure head of the standing liquid.

A second alternative to prevent spontaneous dripping of the liquid out of the outlet valve 4 is to use a plunger 6 with an amount of friction against the inner surface of the reservoir 1 greater than the gravity pressure of the liquid 12. An additional advantage of the plunger 6 is that it prevents spillage of the liquid 12 from the top of the reservoir 1 (which would likely occur if the reservoir were left open from above). In this manner, the plunger will not be drawn downwards inside the reservoir merely by the weight of the liquid. However, when the metering chamber is emptied and a small amount of liquid is drawn from the reservoir 1 to refill the metering chamber, the plunger's friction to the reservoir wall is overcome. The plunger 6 thereby moves downward a distance proportional to the volume of liquid expelled. We have found it useful to apply a thin coat of a lubricant such as petroleum jelly to ensure that the plunger 6 moves smoothly downward within the reservoir.

Any combination of valve opening pressure and plunger friction may be used to prevent dripping, but given the low opening pressure typically found in valves of the type used, friction greater than gravity pressure of the liquid is preferred.

Figure 12:
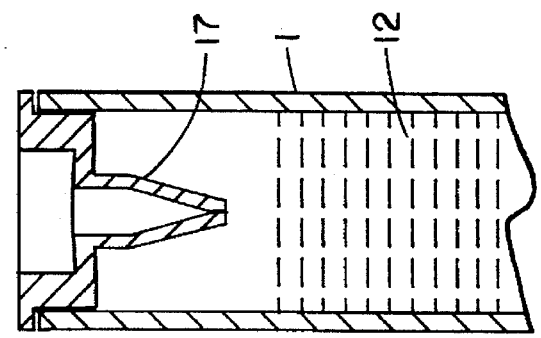

FIG. 12 shows another alternative construction of the cartridge top. Instead of using a plunger, a one-way valve 17 is placed at the top of the reservoir 1. The valve 17 has an opening pressure greater than the gravity pressure of the liquid within the reservoir. This third valve 17 is aligned in the same direction as the metering chamber valves 3 and 4. This allows the entrance of air into the reservoir as liquid is removed. In this case, cracking pressure of any or all of the three valves 3, 4 and 17 prevents spontaneous dripping from the outlet valve. Additionally, the valve 17 prevents spillage of the contents of the reservoir.

Figure 13:
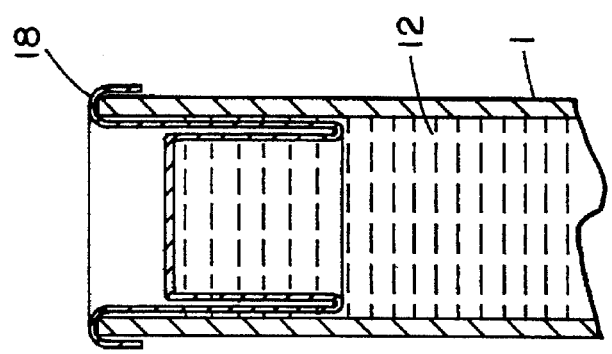

FIG. 13 shows another alternative construction for the top of the cartridge. A rolling diaphragm cover 18 is mounted at the top of the reservoir 1 and is drawn into the reservoir as the liquid is used up. This construction prevents spillage of the liquid 12 as well as provides a seal to prevent air entry.

The rolling diaphragm can be made of any thin flexible elastomer such as natural rubber. The top of the rolling diaphragm can be sealed to the reservoir wall i by stretching the diaphragm over the reservoir, with an adhesive or by heat sealing.

Figure 14:
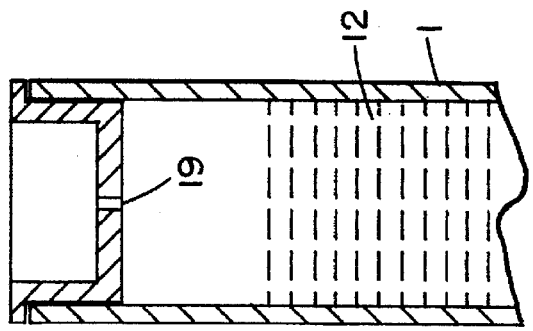
FIGS. 12–14 are cross-sectional views of the uppermost portion of the cartridge reservoir, demonstrating alternative constructions.

FIG. 14 demonstrates a third alternative construction. The top of the reservoir is closed, except for a small aperture 19 for the entrance of air. The diameter of the aperture at the top of the reservoir can be sufficiently small to effectively prevent accidental spillage of the liquid contents of the cartridge but still allow air entry as liquid is dispensed from the cartridge.

A fluid level sensor may be provided adjacent to the cartridge reservoir. For example, a shaft can be connected to the top of the plunger. The shaft can be designed with a shape such that as it is drawn into the cartridge reservoir, it can optically or electrically open or close a circuit at a certain depth within the cartridge reservoir. In this manner, the shaft connected to the plunger can signal to a computer the depth of entry into the cartridge reservoir. The depth of entry would therefore be directly proportional to the amount of liquid remaining in the cartridge reservoir. Such an arrangement provides an automatic means for sensing the amount of liquid remaining inside the reservoir.

A variety of different configurations for the dispensing actuators DA may be used to apply pressure on the metering chamber tubing. Although a push-type of actuator DA is shown in FIG. 1, a rotary or pull-type could also be used with slight modifications to the design, as would be obvious so as to apply a pressure on the metering chamber tubing. Additionally, a solenoid valve could also be used to control pressure to a pneumatic cylinder whose piston rod is the actuator. Alternatively, a piezoelectric transducer may apply the pressure to the metering chamber tubing.

While this invention has been particularly shown and described with references to preferred embodiments thereof, it will be understood by those skilled in the art that various changes in form and details may be made therein without departing from the spirit and scope of the invention as defined by the appended claims. For example, the pump is operable with the metering chamber positioned above the reservoir. Disclosure Document No. 252981 filed May 10, 1990 at the U.S. Patent and Trademark Office shows details of a potential system embodying the present invention.

We claim:

1. A dispensing assembly comprising:
    an assembly base;
    a slide rotor adapted to carry slide frames for holding microscope slides carrying tissue samples and to rotate on the assembly base;
    a plurality of slide frames, each for holding at least one microscope slide, each slide frame comprising a slide frame base supporting a slide and a slide frame housing adapted to fit over the slide frame base with a gasket therebetween to create an individual sealed cavity over each microscope slide for receiving liquid; and
    a reagent rotor adapted to carry different reagents to be applied to selected cavities and rotate on the assembly base.

2. A dispensing assembly as claimed in claim 1, wherein the reagent rotor is adapted to carry a plurality of pump cartridge frames, each comprising at least one receptacle for receiving a cartridge pump containing reagent.

3. A dispensing assembly as claimed in claim 2, wherein each one of the cartridge pumps comprises:
    a reservoir for containing a reagent, the reservoir having an outlet;
    a resilient metering chamber extending below the reservoir and being in fluid communication with the outlet; and
    an outlet valve at a lower end of the resilient metering chamber.

4. A dispensing assembly as claimed in claim 3, further comprising a dispensing station positioned adjacent to the slide rotor and the reagent rotor and in a fixed relationship with the assembly base.

5. A dispensing assembly as claimed in claim 4, wherein the dispensing station comprises an actuator adapted to deform the resilient metering chambers of the cartridge pumps positioned on the reagent rotor to eject a volume of the corresponding reagent through the outlet valve onto a slide held in one of the slide frames on the slide rotor.

6. A dispensing assembly as claimed in claim 4, wherein the dispensing station comprises rinse bottles storing rinsing solutions for rinsing slides on the slide rotor.

7. A dispensing assembly as claimed in claim 4, wherein the dispensing station comprises:
    pressurized rinse bottles;
    rinse tubes extending between the pressurized rinse bottles and a fixed position above the slide rotor to convey rinsing solutions from the rinse bottles to slides underneath ends of the rinse tubes; and
    pinch valves adapted to pinch off the rinse tubes to enable selective conveyance of the rinse solutions to the slides on the slide rotor.

8. A dispensing assembly as claimed in claim 4, wherein the dispensing station comprises a vacuum device for removing liquid covering the slides on the slide rotor.

9. A dispensing assembly as claimed in claim 8, wherein the vacuum device comprises:
    a vacuum bottle;
    a vacuum hose extending from the vacuum bottle; and
    a vacuum hose transport mechanism for bringing the end of the vacuum hose into a cavity above the slides to enable the removal of liquid covering the slides.

10. A dispensing assembly as claimed in claimed in claim 3, wherein each one of the cartridge pumps further comprises an inlet valve at an upper end of the resilient metering chamber, wherein the inlet valve and the outlet valve are one-way valves which are aligned in the same direction to provide unidirectional reagent flow through the resilient metering chamber.

11. A dispensing assembly as claimed in claim 3, further comprising an actuator adapted to deform the resilient metering chambers of the cartridge pumps positioned on the reagent rotor to eject a volume of the corresponding reagent through the outlet valve onto a slide held in one of the slide frames on the slide rotor.

12. A dispensing assembly as claimed in claim 1, wherein the slide rotor and the reagent rotor rotate on the same axis.

13. A dispensing assembly as claimed in claim 1, wherein the slide frames are radially insertable into the slide rotor.

14. A dispensing assembly as claimed in claim 1, wherein each slide frame base comprises heating units for heating each one of the slides.

15. A dispensing assembly as claimed in claim 1, wherein each slide frame further comprises a temperature detector for detecting a temperature of at least one of the slides.

16. A dispensing assembly as claimed in claim 1 further comprising a vacuum device for removing liquid covering the slides on the slide rotor.

17. A dispensing assembly as claimed in claim 16 wherein the reagent rotor is adapted to carry a plurality of pump cartridges adapted to dispense reagent into the cavities.

18. A dispensing assembly comprising:

an assembly base;

a slide rotor adapted to carry slide frames for holding slides carrying tissue samples and to rotate on the assembly base;

a reagent rotor adapted to carry a plurality of cartridge pumps containing reagents and to rotate on the assembly base, each cartridge pump comprising:

a reservoir for containing a reagent, the reservoir having an outlet;

a resilient metering chamber extending below the reservoir and being in fluid communication with the outlet; and an outlet valve at a lower end of the resilient metering chamber;

a dispensing station positioned adjacent to the slide rotor and the reagent rotor and in a fixed relationship with the assembly base, the dispensing station comprising rinse bottles storing rinsing solutions for rinsing slides on the slide rotor.

19. A dispensing assembly comprising:

an assembly base;

a slide rotor adapted to carry slide frames for holding slides carrying tissue samples and to rotate on the assembly base;

a reagent rotor adapted to carry a plurality of cartridge pumps containing reagents and to rotate on the assembly base, each cartridge pump comprising:

a reservoir for containing a reagent, the reservoir having an outlet;

a resilient metering chamber extending below the reservoir and being in fluid communication with the outlet; and an outlet valve at a lower end of the resilient metering chamber; and a dispensing station positioned adjacent to the slide rotor and the reagent rotor and in a fixed relationship with the assembly base, the dispensing station comprising:

pressurized rinse bottles;

rinse tubes extending between the pressurized rinse bottles and a fixed position above the slide rotor to convey rinsing solutions from the rinse bottles to slides underneath ends of the rinse tubes; and pinch valves adapted to pinch off the rinse tubes to enable selective conveyance of the rinse solutions to the slides on the slide rotor.

\* \* \* \* \*

UNITED STATES PATENT AND TRADEMARK OFFICE
CERTIFICATE OF CORRECTION

PATENT NO.     : 5,645,114
DATED          : July 8, 1997
INVENTOR(S)    : Steven A. Bogen and Herbert H. Loeffler It is certified that error appears in the above-identified patent and that said Letters Patent is hereby corrected as shown below:

Column 1,
Line 8, insert the following:

-- GOVERNMENT SUPPORT
     This invention was made with government support under Grant Number 2R44AI 29778-02 awarded by the National Institutes of Health. The government has certain rights in the invention. --

Signed and Sealed this

Thirtieth Day of October, 2001

*Attest:*

NICHOLAS P. GODICI
*Acting Director of the United States Patent and Trademark Office*

*Attesting Officer*